United States Patent [19]
Müller et al.

[11] Patent Number: 5,922,891
[45] Date of Patent: Jul. 13, 1999

[54] 2-SUBSTITUTED 1,8-DIHYDROXY-9(10H)-ANTHRACENONE PHARMACEUTICALS

[75] Inventors: Klaus Müller; Helge Prinz, both of Regensburg; Wolfgang Wiegrebe, Zeitlarn, all of Germany

[73] Assignee: Teva Pharmaceutical Industries Ltd., Netanya, Israel

[21] Appl. No.: 08/933,926

[22] Filed: Sep. 19, 1997

Related U.S. Application Data

[63] Continuation of application No. 08/480,102, Jun. 7, 1995, abandoned.
[51] Int. Cl.$^6$ .................................................. C07C 50/16
[52] U.S. Cl. .................................... 552/290; 514/570
[58] Field of Search ............................ 552/290; 514/570

[56] References Cited

PUBLICATIONS

B. Bonnekoh, et al., *Arch. Pharm.* (*Weinheim*) 324, 899–906 (1991).
Mueller, at al., Arch. Pharm. (Weinheim, Ger.), 320: 59–66 (1987).
Tranzer, et al., Arch. Pharm. (Weinheim, Ger.), 321: 447–449 (1988).
Mueller, et al., J. Med. Chem., 37: 1660–1669 (1994).
Finnen, M.J., Lancet II, 1129–1130 (1984).
Mueller, et al., Biochem. Pharmacol., 46: 1695–1704 (1993).
Corey et al, J. Am. Chem. Soc., 106: 1503–1504 (1984).
Takahashi, I et al, ChemPharm. Bull (1982) 30(12) 4539–44.
CA 116:50897 (1991).

*Primary Examiner*—Paul J. Killos
*Attorney, Agent, or Firm*—Kenyon & Kenyon

[57] ABSTRACT

2-substituted 1,8-dihydroxy-9(10h)-anthracenones, therapeutic compositions containing at least one novel 2-substituted 1,8-dihydroxy-9(10h)-anthracenone compound and methods of treating inflammatory conditions are provided.

20 Claims, No Drawings

2-SUBSTITUTED 1,8-DIHYDROXY-9(10H)-ANTHRACENONE PHARMACEUTICALS

This application is a continuation of U.S. Ser. No. 08/480,102, filed Jun. 7, 1995, now abandoned.

FIELD OF THE INVENTION

This invention relates to anthracenone compounds useful in the treatment of allergic and inflammatory conditions and therapeutic compositions containing such compounds. In particular, the invention relates to 2-substituted 1,8-dihydroxy-9(10H)-anthracenone compounds and compositions containing same. The invention also relates to methods of treating allergic and inflammatory conditions.

BACKGROUND OF THE INVENTION

Inflammation in the body occurs in response to numerous conditions including, for example, physical injury, allergy, tumor growth, certain disease states, chemical damage and microbial infection. Representative of local effects that can occur are increased vascular permeability, release of degradative enzymes, migration to the affected site by leukocytes, neutrophil burst response to destroy invading cells and secretion of cytokines. There is considerable interest in the development of therapeutic compounds and compositions capable of controlling inflammation.

Psoriasis is a common chronic inflammatory and proliferative skin disease, characterized by increased cell proliferation at affected sites. At the molecular level, psoriasis is characterized by an abnormal metabolism of an arachidonic acid, particularly in the lipoxygenase pathways. Lesional skin contains increased functional responses of neutrophils. See, for example, Bedord, et al., J. Invest. Dermatol, 85:30 (1983); Schroder, et al., J. Invest. Dermatol, 85:30 (1985); and Schroeder, J. M., Invest. Dermatol., 86:331 (1986). However, anthralin therapy is associated with several unpleasant side effects including increased inflammation and irritation of non-effected skin surrounding treated lesions.

There is substantial evidence that generation of free radicals (Finnen, M. J., Lancet II, 1129–1130 (1984) and, Shroot, et al., Arzneim.-Forsch./Drug Res., 36:1253–1255 (1986)) and active oxygen species (Muller, et al., Arch Pharm (Weinheim), 320: 59–66 (1987); Muller, et al., Biochem. Pharmacol., 37:4277–4280 (1988); Muller, et al., Biochem. Pharmacol, 46:1695–1704 (1993); and Muller et al., Arzneim-Forsch/Drug Res., 41:1176–1181 (1991)) play a key role in both the activity and side effects caused by anthralin.

Anthralin has been demonstrated to produce superoxide radicals by one electron reduction of oxygen (Muller, et al., Arch. Pharm. (Weinheim, Ger.), 320: 59–66 (1987)). There is evidence that iron plays a significant role in superoxide radical production by antipsoriatic anthrones in vivo. The significant production of superoxide radicals requires the presence of a transition metal, such as iron, since the direct reaction of oxygen with biomolecules is spin forbidden (Miller, et al., Free Radical Biol. Med, 8: 95–108 (1990)). Moreover, superoxide radicals readily undergo dismutation to form hydrogen peroxide and oxygen, which have only moderate reactivity and therefore, cannot be responsible for the biological damage observed in systems in which they are generated (Fridovich, I., Arch. Biochem. Biophys., 247:1–11 (1986)). It has been suggested, therefore, that the observed biological damage is due to the formation of hydroxyl radicals (Halliwell, et al., Methods Enzymol., 186:1–85 (1990)), which may be catalyzed by ferrous iron via the Haber-Weiss cycle, a superoxide-driven Fenton reaction (Gutteridge, et al., Biochem. J., 199:268–265 (1981). Morever, iron has been demonstrated to play a key role in the formation of hydroxyl radicals by anthralin (Muller, et al., Biochem. Pharmacol; 37:4277–4280 (1988); Muller, et al., Biochem. Pharmacol, 46:1695–1704 (1993)) and has been suggested to be the most likely candidate for catalyzing hydroxyl radical generation in vivo (Halliwell, et al., Methods Enzymol., 186:1–85 (1990)). biological damage is due to the formation of hydroxyl radicals (Halliwell, et al., Methods Enzymol., 186:1–85 (1990)), which may be catalyzed by ferrous iron via the Haber-Weiss cycle, a superoxide-driven Fenton reaction (Gutteridge, et al., Biochem. J., 199:268–265 (1981). Morever, iron has been demonstrated to play a key role in the formation of hydroxyl radicals by anthralin (Muller, et al., Biochem. Pharmacol; 37:4277–4280 (1988); Muller, et al., Biochem. Pharmacol, 46:1695–1704 (1993)) and has been suggested to be the most likely candidate for catalyzing hydroxyl radical generation in vivo (Halliwell, et al., Methods Enzymol., 186:1–85 (1990)).

Further evidence in support of the role of iron in catalyzing superoxide formation includes documentation of enhancement of anthralin-induced lipid peroxidation in the presence of iron (Muller, et al., Biochem. Pharmacol., 46:1695–1704 (1993)), suggesting that iron mediates oxidative damage caused by anthralin and other anti-psoriatic anthrones. Moreover, iron is excreted by skin cells and the level of iron excretion increases at the site of psoriatic lesions (Trenam, et al., J. Invest., Dermatol., 99:674–682 (1992)).

It has been proposed that administration of 5-lypoxygenase inhibitors may be therapeutically useful for treatment of inflammatory conditions, including psoriasis. However, some inflammatory conditions, such as psoriasis involve both inflammatory and hyperproliferative process. Consequently, compounds that are targeted toward only one aspect of the disease are unlikely to be totally beneficial. There exists, therefore, a need for anti-inflammatory agents capable of inhibiting lipoxygenase pathways of arachidonic acid metabolism to thereby inhibit the proliferative activity of the products of lipoxgenase pathways e.g., 5-HETE and $LTB_4$, while simultaneously suppressing iron-dependent generation of oxygen radicals.

SUMMARY OF THE INVENTION

In one aspect of the present invention there is provided a novel 2-substituted 1,8-dihydroxy-9(10H)-anthracenone compound having the following structural formula (I)

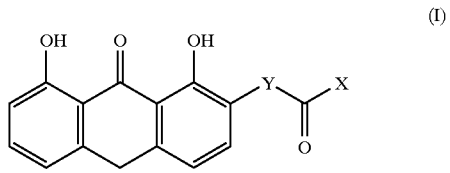

wherein Y represents a linear or branched chain alkylene group having 1 to 10 carbon atoms, a phenylalkylene group having 7 to 10 carbon atoms, or a phenylacylene group having 7 to 10 carbon atoms; an imino group, or an imino group substituted with a linear or branched chain alkyl group having 1 to 10 carbon atoms; and X represents a hydroxyl group, an oxygen substituted with a branched or straight chain alkyl group having 1 to 10 carbon atoms, an amino group, amino group substituted with a straight or branched chain alkyl group having 1 to 10 carbon atoms, a hydroxylamine group, or an N-alkyl substituted hydroxylamine, said N-alkyl having 1 to 10 carbon atoms, with the proviso that when X is hydroxyl, Y is not an alkyl group having 1 to 3 carbon atoms or 4-CH$_2$ Phenyl.

In another aspect of the invention there is provided an anti-inflammatory composition comprising a therapeutically effective amount of at least one compound of formula (I) as defined above, and a pharmaceutically acceptable carrier. In a preferred embodiment of the invention the anti-inflammatory composition comprises at least one compound having the structural formula (I) wherein Y represents a linear or branched chain alkyl group having 1 to 6 atoms and X represents —N(CH$_3$)OH.

In another aspect of the invention, there is provided a method for treating an inflammatory condition in a patient in need thereof comprising administering to said patient a composition comprising a therapeutically effective amount of at least one compound of formula (I) as defined above and a pharmaceutically acceptable carrier.

In yet another aspect of the invention there is provided a method of treating psoriasis in a patent in need thereof comprising topically applying a therapeutically effective amount of a composition comprising at least one compound of formula (I) as defined above and a pharmaceutically acceptable carrier to the skin of said patient in an area in need of treatment.

DETAILED DESCRIPTION OF THE INVENTION

The compounds of the invention have the following structural formula

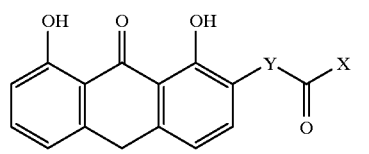

(I)

wherein Y represents a linear or branched chain alkylene group having 1 to 10 carbon atoms, a phenylalkylene group having 7 to 10 carbon atoms, a phenylacylene group having 7 to 10 carbon atoms, an imino group, or an imino group substituted with a linear or branched chain alkyl group having 1 to 10 carbon atoms, and X represents a hydroxyl group, an oxygen substituted with a straight or branched chain alkyl group having 1 to 12 carbon atoms, an amino group, amino group substituted with a straight or branched chain alkyl group having 1 to 12 carbon atoms, a hydroxylamine group, or an N-alkyl substituted hydroxylamine, said N-alkyl being straight or branched chain and having 1 to 12 carbon atoms, with the provision that when X is hydroxyl, Y is not an alkyl group having 1 to 3 carbon atoms or 4-CH$_2$ phenyl.

The compounds of the invention contain an iron chelating functionality attached to a 1,8-dihydroxy-9(10H)-anthracenone pharmacophore by a side chain. More specifically, the iron chelating functionality is a hydroxamic acid or carboxylic acid moiety.

Iron has been shown to play a role in the activity of 5-lipoxygenase (Musser, et al., J. Med. Chem., 35:2501–2524 (1994). Moreover, hydroxamic acid analogues of arachidonic acid are effective inhibitors of 5-lipoxygenase (LO) (Corey, et al., J. Am. Chem. Soc. 106:1503–1504 (1984)). Consequently, there have been attempts to develop therapeutic agents, particularly antipsoriatic agents that are hydroxamic acid based 5-LO inhibitors. Although a number of anti-psoriatic agents that interfere with the 5-LO pathway have been formulated these compounds do not address both the inflammatory and hyperproliferative aspects of the disease.

In contrast, the compounds of the present invention contain a hydroxamic acid or carboxylic acid moiety, which functions as an iron chelating agent and in this manner effectively inhibits 5-LO. The present compounds also contain an anthracenone pharmacophore. The combination of the hydroxamic acid moiety or ester with the anthracenone results in significantly decreased cell proliferation associated with psoriasis and other inflammatory conditions, as well as decreased 5-LO activity.

Numerous studies directed to the use of anthracenone compounds as antpsoriatic agents suggest that the mechanism of action of these compounds involves free radicals and active oxygen species. However, free radical and active oxygen generation by these compounds is also thought to be responsible for the unwanted side effects caused by their use, e.g. local inflammation and irritation. Accordingly, a characteristic of the present 2-substituted-anthracenone compounds is that the therapeutic effects obtained therewith, eg. decreased inflammation and decreased hyperproliferation are obtained at low dosage concentration of the compound with a concomitant minimalization of side effects.

Preferred compounds of the invention are exemplified below in Table 1. Compounds exhibiting the highest biological activity, e.g. 5-LO inhibition, antiproliferative effect, dideoxyribose degradation and/or inhibition of lipid peroxidation at low concentration are most preferred compounds of the invention. In particular, hydroxamic acid or 2-N-methyl hydroxamic acid substituted-1,8-dihydroxy-9(10H) anthracenone compounds are preferred compounds of the invention, with compounds wherein X is —N(CH$_3$) OH and Y is (CH$_2$)$_2$, (CH$_2$)$_3$, (CH$_2$)$_4$ or (CH$_2$)$_5$ being most preferred compounds.

As aforementioned, the compounds of the invention are useful as therapeutic agents in the treatment of inflammatory conditions, such as psoriasis, eczema, contact dermatitis, and seborrhea. For example, the present compounds, when provided to a patient in a therapeutically effective amount inhibit lipoxygenase activity and other inflammatory processes, including hyperproliferation of cells at an affected area, such as at the site of skin lesions. Moreover, side effects such as inflammation and irritation at the site of application of the present therapeutic compounds are minimal.

Many of the compounds according to the invention exhibit both potent 5-LO and keratinocyte growth inhibitory activity (antiproliferative activity) and their activities against both aspects of psoriasis are attributed to the hydroxamic acid functionality. The corresponding carboxylic acid containing compounds of the invention exhibit little activity against keratinocyte growth but are active as 5-LO inhibitors. The corresponding ester containing compounds of the invention are not as active as 5-LO inhibitors, however, they exhibit antiproliferative activity.

The compounds of the invention may be used to treat inflammatory conditions, such as, for example, psoriasis, allergy and contact dermatitis. The compounds when incorporated into a pharmaceutical or cosmetic composition in therapeutically effective amounts are useful in human and veterinary medicine, and particularly for the treatment of psoriasis or contact dermatitis.

According to one aspect of the invention the compounds as defined hereinafter are incorporated into pharmaceutical or cosmetic compositions singly or in combinations thereof at a concentration of about 0.01% to 20% by weight per compound, preferably between 0.1 and 5% by weight per compound and most preferably between 0.2% and 3% by weight per compound in a pharmaceutically acceptable or cosmetically acceptable carrier for topical application. For intravenous, intramuscular, intradermal, subcutaneous, intra- or peri-lesional application of the compounds, the composition of the invention is preferably formulated to contain about 10 to 100 milligrams, and most preferably to contain about 20 to 50 milligrams of the compound in a solution or suspension of a pharmaceutically acceptable carrier, such as for example, sterile saline or sterile water. Precise concentration of the compound in any composition of the invention can be determined according to routine medicine practice.

The compositions of the invention may also be formulated for enteral administration in the form of, for example, tablets, granules, gels, capsules, syrups, suspensions, and powders.

Alternatively, the compositions of the invention may be applied rectally in the form of a dissolvable suppository, or sublingually, transdermally, and so forth. For transdermal application it is preferable to include a skin penetrating adjuvant, such as, for example, dimethyl sulfoxide (DMSO), dimethyl acetemide, etc.

The compositions of the invention may contain additional inert or other pharmacologically active adjuvant, such as a binder, filler, diluent, thickening agent, preservative, anti-irritant agent, emollient, moisturizing agent, and combinations thereof. These pharmaceutical or cosmetic forms of the compositions of the present invention are prepared in accordance with conventional procedures.

Preferably, the composition of the invention is formulated for topical application as an ointment, ungent, tincture, aerosol, solution, cream, lotion, paste, jelly, spray, bath oil, shampoo suspension, micronized powder and the like. The pharmaceutical cosmetic carrier of such topically applied compositions may be, for example, lanolin, petroleum, polyethylene glycol or alcohol.

In a preferred embodiment of this aspect of the invention the composition is formulated to contain at least one compound of the invention that exhibits both antipoliferative activity and anti-5-LO activity. It is also within the scope of the invention to formulate compositions containing a combination of compounds of the invention, and preferably the combination of compounds provides a composition that exhibits both anti-proliferative and anti-LO effects. For example, the combination of an ester compound of the invention with a carboxylic acid compound of the invention provides both anti-proliferative and anti-LO activity.

Treatment of a patient with a composition of the invention is carried out for a period of time required to prevent, reverse or alleviate the medical condition or control clinical symptoms. The treatment regimen will vary depending on such factors as the particular inflammatory condition to be treated, severity of symptoms, route of administration, etc. Typically, for topical administration of a composition of the invention to treat psoriasis or contact dermititis for example, treatment is carried out at least once per day until symptoms are visibly eliminated. Most preferably, in the topical treatment of psoriasis or contact dermatitis the composition is applied in sufficient amount to cover the affected area, i.e. applied directly to skin lesions, several times per day until such time that the lesions are no longer detectable.

If desired the composition of the invention may be incorporated into a bandage or other wound dressing to provide continuous exposure of the dressed wound to the therapeutic compound.

The synthesis of the compounds according to the invention can be represented by the following reaction scheme I:

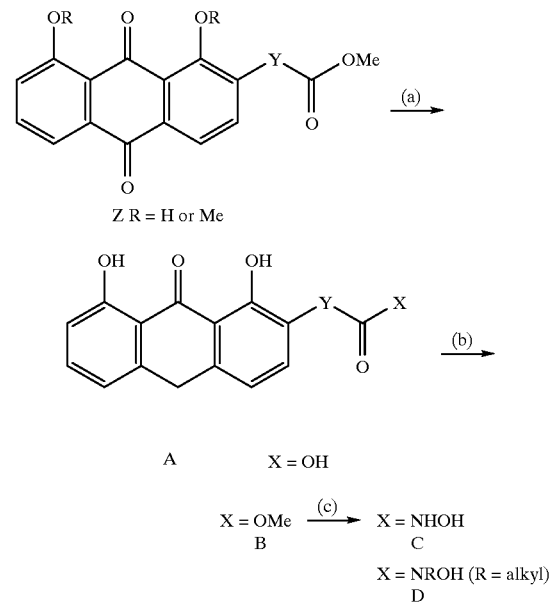

In general 1,8-dihydroxy-9(10H)-anthracenone carboxylic acids (A) may be prepared from an appropriately 2-substituted 9,10-anthracenedione methyl carboxylate (Z) by reduction in glacial acetic acid at 118° C. with $SnCl_2$/ HCL, according to the method of Auterhof, H. and Scherff, F. C., Arch Pharm (Weinheim, Ger) 293, 918–925 (1960). Esterification of the 1,8-dihydroxy-9(10H)-anthracenone carboxylic acid (A) gives the 2-substituted 1,8-dihydroxy-9(10H)-anthracene methyl carboxylate (B). The 2-substituted 1,8-dihydroxy-9(10H)-anthracenone hydroxamic (C) or N-alkylhydroxamic acid (D) are prepared by reacting hydroxylamine hydrochloride or an appropriately substituted hydroxylamine hydrochloride according to conventional methods. The required 2-substituted 1,8-dihydroxy-, 1-hydroxy-8-methoxy-, or 1,8-dimethoxy-8-10-anthracenedione methyl carboxylate (Z) is prepared by esterification of the corresponding carboxylic acid, which in turn is obtained either according to literature methods, such as, for example, Tanzer, H. et al., Arch Pharm (Weinheim, Ger) 447–449 (1988), (Compounds 1A–D and IIA–D of Table 1), or as exemplified in Schemes II–VI below and described in further detail below.

Scheme II.

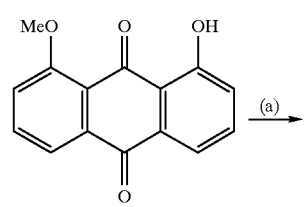

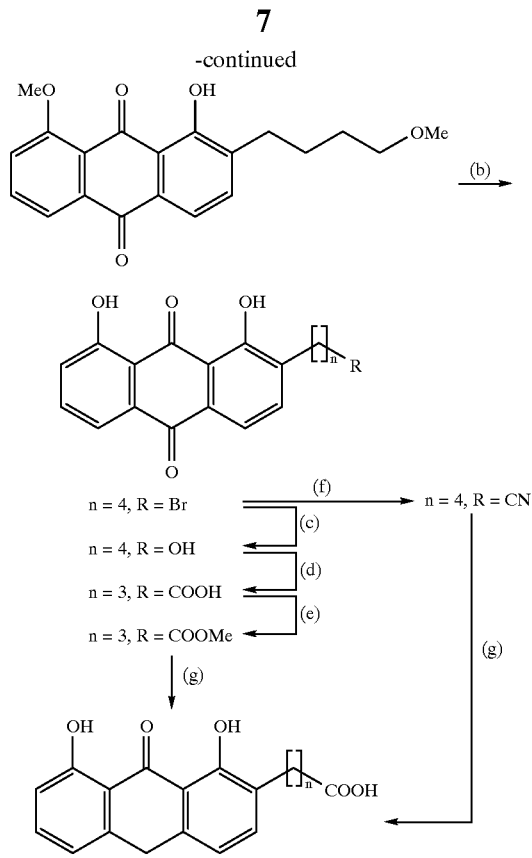

Reagents: (a) $Na_2S_2O_4$, NaOH, $H_3CO(CH_2)_3CHO$, $N_2$, 90° C.; (b) HBr 62%, glacial acetic acid, 118° C.; (c) hexamethylphosphortriamide/$H_2O$, 128° C.; (d) pyridinium dichromate, DMF, room temperature; (e) MeOH, concentrated $H_2SO_4$; (f) NaCN, DMSO; (g) $SnCl_2$, HCl, glacial acetic acid, 118° C.

Scheme III.

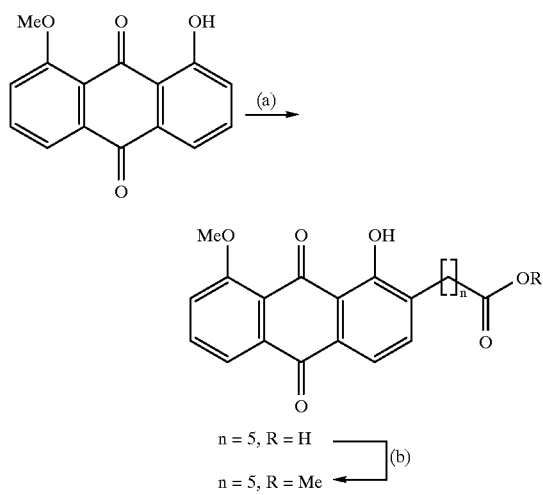

Reagents: (a) $Na_2S_2O_4$, NaOH, $OCH(CH_2)_4COOMe$, $N_2$, 90° C.; (b) MeOH, concentrated $H_2SO_4$.

Scheme IV.

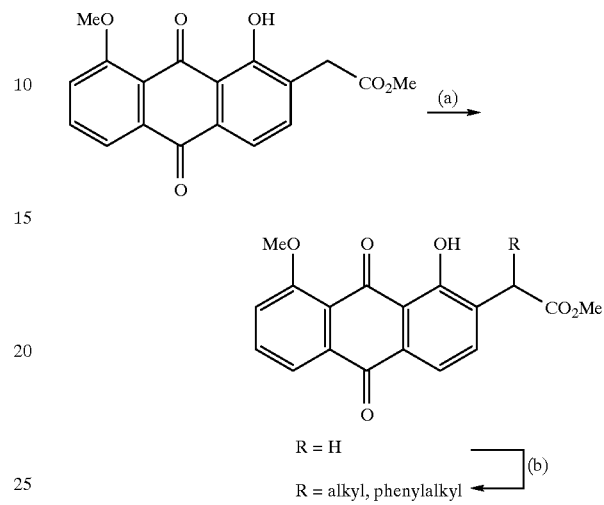

Reagents: (a) $(Me)_2SO_4$, $K_2CO_3$, acetone (b) R-I or R-Br, NaH/THF or NaH/DMSO, respectively, $N_2$.

Scheme V.

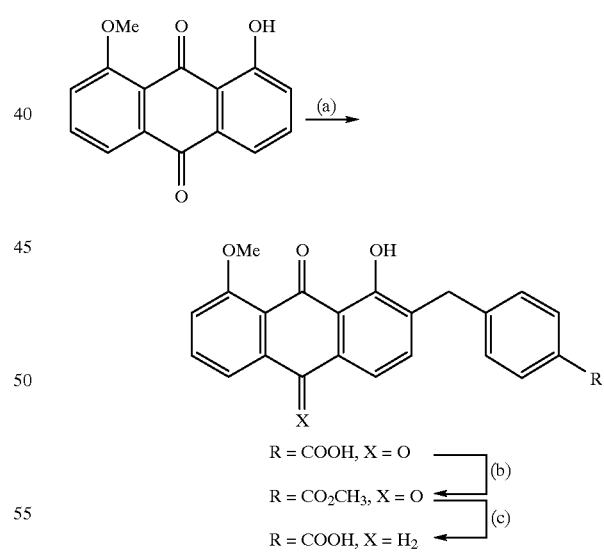

Reagents: (a) $Na_2S_2O_4$, MeOH, NaOH, $HOOCC_6H_5CHO$, $N_2$, 90° C.; (b) MeOH, concentrated $H_2SO_4$; (c) $SnCl_2$, HCl, glacial acetic acid, 118° C.

Scheme VI.

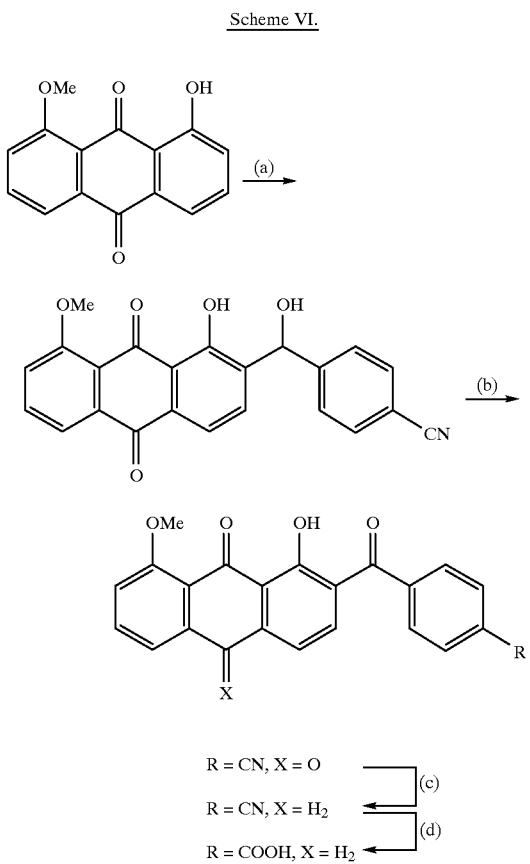

Reagents: (a) NCC₆H₅CHO, N₂, 0–5° C., (b) pyridinium chromate, DMF, room temperature; (c) SnCl₂, HCl, glacial acetic acid, 118° C.; (d) water, concentrated H₂SO₄, glacial acetic acid, 118° C.

SYNTHESIS OF STARTING MATERIALS SCHEME (II)

Synthesis of Compounds IIIA–D (Table 1):

1. 1-Hydroxy-8-methoxy-4-[1-(4-methoxybutyl)]-9,10-anthracenedionoe(IIIv). This compound was prepared from 1-hydroxy-8-methoxy-9,10-anthracenedione and 4-methoxybutyraldehyde, Stetter, H. and Leinen, H. T., *Chem Ber* 116, 254–263 (1983), according to the method described for Vy below: orange crystals (5.3 g, 40%); mp 139° C.

2. 4-[1-(4-Bromobutyl)]-1,8dihydroxy-9,10-anthracenedione] (IIIw). A suspension of IIIv (5.00 g, 14.69 mmol) in glacial acetic acid (100 mL), and heated to reflux. To the resulting solution was added dropwise 62% HBr (50 mL), and the solution was refluxed for 3 h. The solution was then cooled to room temperature and water (50 mL) was added. After 30 minutes the precipitate was filtered by suction followed by washing with water (4×50 mL). The residue was dried under vacuum at 50° C., and chromatography using methylene chloride afforded orange-yellow crystals (4.70 g, 85%): mp 125° C. (decomp.).

3. 4-[(9,10-Dihydro-1,8-dihydroxy-9,10-dioxo-2-anthracene)butan-1-ol] (IIIx). A suspension of IIIw (4.50 g, 11.99 mmol) was suspended in a solution of 15% water in hexamethyl phosphorous triamide (50 mL), and the temperature was slowly raised to 130° C. The mixture was stirred at 130° C. for 6 hours (TLC control), then cooled to room temperature, poured into water (1 L), and extracted with ether (3×200 mL). The combined organic phase was washed with water (3×400 mL) and dried over Na₂SO₄, evaporated and purified by chromatography using ether to give orange crystals: mp 149° C.

4. 4-[(9,10-Dihydro-1,8-dihydroxy-9,10-dioxo-2-anthracene)butanoic acid] (IIIy). A solution of IIIx (200 g, 6.40 mmol) in dry dimethylformamide (25 mL) and pyrdinium dichromate (9.64 g, 25.61 mmol) was stirred at room temperature for 6 hours. The solution was poured into water (500 mL) and the product was extracted with methylene chloride (4×100 mL). The combined organic phase was washed with water (4×200 mL), dried over Na₂SO₄, and evaporated. The resulting residue (60 mL) was treated with a small amount of petroleum ether (40-60), shaken thoroughly, and allowed to sand at 0° C. The precipitate was filtered by suction and the crude product was used in the subsequent esterification step.

5. Methyl 4-[(9,10-Dihydro-1,8-dihydroxy-9,10-dioxo-2-anthracene)butanoate] (IIIz).] A suspension of IIIy in methanol (500 mL) and 96% sulfuric acid (5 mL) was refluxed for 24 hours. The reaction mixture was cooled to room temperature, kept at 0° C. for 2 hours, then filtered by suction, washed with precooled methanol (100 mL), and dried under vacuum. The residue was purified by chromatography using methylene chloride to give orange crystals: mp 135° C.

6. 5-[(9,10-Dihydro-1,8-dihydroxy-9,10-dioxo-2-anthracene) valeronitrile (IVz). Sodium cyanide (1.10 g, 22.5 mmol) was suspended in dry dimethyl sulfoxide (40 mL) and heated to 90° C. (oil bath). The oil bath was removed and to the resulting solution was added slowly a solution of IIIw (1.69 g, 4.50 mmol) in dimethyl sulfoxide (15 mL). The solution was stirred unitl the reaction was completed (TLC control). The solution was poured into water (500 mL) and the product was extracted with methylene chloride (3×50 mL). The combined organic phase was washed with water (3×100 mL), dried over Na₂SO₄, and evaporated. The resulting residue was purified by chromatography using methylene chloride to give orange crystals (0.90 g, 62%): mp 175° C. IVA was obtained from IVz as described in Example 1 below.

SCHEME (III)

Compounds VA–D

1. Methyl 6-Oxohexanoate. This compound was prepared similarly to the method of Huckstep and Taylor, *Synthesis* 881–882 (1982). The crude product was used in the subsequent reaction.

2. 6-[9,10-Dihydro-1-hydroxy-8-methoxy-9,10-dioxo-2-anthrancene) hexanoic acid (Vy). To a solution of NaOH (12 g, 0.30 mol) in water (600 mL) was added 1-hydroxy-8-methoxy-9,10-anthracenedione, Krohn, K. and Baltus, W., *Liebigs Ann Chem* 1579–1581 (1982), (100 g., 39.5 mmol), and the solution was stirred for 15 minutes at 40° C. A solution of Na₂S₂O₄ (12 g, 58.5 mmol) in water (50 mL) was added under nitrogen. The solution was stirred and heated to 70° C. for 15 minutes. Methyl 6-oxohexanoate (10 g, 68.4 mmol) in 2 N NaOH (50 mL) was added, and the temperature was raised to 90° C. The reaction mixture was stirred for 12 h (TLC control) under nitrogen, then cooled to room temperature, and aerated for 45 min. Water was added (500 mL), the mixture was acidified by 2 N HCl until it turned orange, and stirred for 20 min. The precipitate thus obtained was filtered by suction, washed with water (1 L), and the residue was refluxed in toluene (1 L) for 2 hours at a Dean-Stark trap. The mixture was then cooled to room temperature and kept at 0° C. for 2 h. Suction filtration followed by washing with small amounts of petroleum ether (40-60) and drying under vacuum afforded the crude product which was used in the subsequent esterifcation step.

3. Methyl 6-[(9,10-Dihydro-1-hydroxy-8-methoxy-9,10-dioxo-2-anthracene) hexanoate (Vz). This compound was prepared from Vy as described for IIIz (Scheme II) and gave orange crystals: mp 104° C.

SCHEME (IV)

Compounds VIIA–D:

1. Methyl [(9,10-Dihydro-9,10-dioxo-1-hydroxy-8-methoxy-2-anthracene)] acetate (VIIx). This compound was prepared from [(9,10-dihydro-1-hydroxy-8-methoxy-9,10-dioxo-2-anthracene) acetic acid, Tanzer, H. et al., *Arch Pharm* (Weinheim, GER) 321, 447–449 (1988), as described for IIIz (Scheme II) and gave orange crystals: mp 159° C.

2. Methyl [(9,10-Dihydro-1,8-dimethoxy-9,10-dioxo-2-anthracene)]acetate (VIIy). To a suspension of VIIx (8.50 g, 11.30 mmol) and sodium carbonate (13.82 g, 100 mmol) in dry acetone (500 mL) heated to reflux was added, dropwise over 1 hour, dimethyl sulfate (69.37 g, 55 mmol). The reflux was continued until the reaction mixture turned yellow (6 hours). The reaction was then cooled to room temperature, filtered by suction, washed with acetone (500 mL), and evaporated. The residue was washed with petroleum ether (40-60), dried, and recrystallized from methylene chloride to give yellow crystals; mp 134° C.

3. Methyl 2-[(9,10-Dihydro-1,8-dimethoxy-9,10-dioxo-anthracene)] propionate (VIIz). A suspension of VIIy (2.00 g, 5.88 mmol) in absolute tetrahydrofuran and 60% sodium hydride (0.50 g, 20.83 mmol) in paraffin oil was stirred at room temperature for 20 minutes. Then methyl iodide (1.14 g, 8.00 mmol) was added dropwise, and the mixture was stirred until the reaction was completed (TLC control). The reaction mixture was poured into a mixture of ice-water (500 g) and 37% HCl (20 mL), and the product was extracted with ether (4×150 mL). The combined organic phase was washed with water (3×150 mL), dried over $Na_2SO_4$, and evaporated. The resulting residue was purified by chromatography using ether to give yellow crystals: mp 109° C.

Compounds VIIIA–D (Scheme IV):

Methyl 2-[(9,10-Dihydro-1,8-dimethoxy-9,10-dioxo-2-anthracene)-3-methylbutanoate (VIIIz). This compound was prepared from VIIy (2.00 g, 5.88 mmol) in dimethyl sulfoxide and 2-bromopropane (0.98 g, 8.00 mmol) as described for VIIz and gave yellow crystals: mp 128° C.

Compounds IXA–D (Scheme IV)

Methyl 2-[(9,10-Dihydro-1,8-dimethoxy-9-oxo-2-anthracene)]-3-phenylpropionate (IXz). This was prepared from VIIy (2.00 g, 5.88 mmol) in dimethyl sulfoxide and benzyl bromide (1.37 g, 8.00 mmol) as described for VIIz and gave yellow crystal.

1. Methyl 2-[9,10-Dihydro-1,8-dimethoxy-9,10-dioxo-2-anthracene)-4-phenylbutanoate (Xz). This compound was prepared from VIIy (2.00 g, 5.88 mmol) in dimethyl sulfoxide and 1-phenylethyl bromide (1.48 g, 8.00 mmol) as described for VIIz and gave yellow crystals: mp 112° C.

SCHEME V

Compounds XIA–D: Müller, K. et al., *J Med Chem* 37, 1660–1669 (1994), which is incorporated in its entirety herein, describes synthesis scheme V, which was used to synthesize compounds XIA–D.

SCHEME VI

Compounds XIIA–D:

1. 2-[(4-Cyanophenyl)-1-hydroxy-8-methoxy-hydroxymethyl]-9,10-anthracenedione] (XIIx). To a solution of NaOH (12 g, 0.30 mol) in methanol (600 mL) was added 1-hydroxy-8-methoxy-9,10-anthracenedione, Kron, K. Baltus, W., *Liebigs Ann Chem* 1579–1581 (1982), (10 g, 39.5 mmol), and the solution was stirred at room temperature for 10 minutes. A solution of $Na_2S_2O_4$ (12 g, 58.5 mmol) in water (50 mL) was added under nitrogen, and the solution turned yellow-brown. The solution was then cooled to 0–5° C. and stirred for 30 minutes. 4-Cyanobenzaldehyde (12 g, 91.51 mmol) in tetrahydrofuran (50 mL) was added dropwise, and the reaction mixture was allowed to stir at 0–5° C. for 12 hours under nitrogen. The mixture was aerated for 45 minutes, poured into water (500 mL), and acidified by 2 N HCl until it turned orange. The product was extracted with methylene chloride (4×200 mL). The combined organic phase was washed with water (3×500 mL), dried over $Na_2SO_4$, and evaporated. The resulting residue was purified by chromatography using methylene chloride/methanol (99-1) to give orange crystals: mp 223° C.

2. 2-[(4-Cyanophenyl)-oxomethyl]-1-hydroxy-8-methoxy-9,10-anthracenedione (XIIy). A solution of XIIx (2.00 g, 5.19 mmol) in dry dimethyl formamide (25 mL) and pyridinium dichromate (7.81 g, 20.76 mmol) was stirred at room temperature for 1 hour. The mixture was poured into water (500 mL) and the product was extracted with methylene chloride (3×100 mL). The combined organic phase was washed with water (4×200 mL), dried over $Na_2SO_4$, and evaporated. The resulting residue was purified by chromatography using methylene chloride/methanol (99-1) to give orange crystals: mp 218° C. (decomp.).

3. 2-[(4-Cyanophenyl)-oxomethyl]-1,8-dihydroxy-9(10H)-anthracenone (XIIz). This compound was prepared from XIIy as described in Example I below.

4. 4-[(9,10-Dihydro-1,8-dihydroxy-9-oxo-2-anthracene) oxomethyl]benzoic acid (XIIA). A suspension of XIIz (0.20 g, 0.52 mmol) in water (15 mL), 96% sulfuric acid (10 mL), and glacial acetic acid (10 mL) was refluxed for 3 days (TLC control). Then the mixture was cooled to room temperature, treated with water (10 mL), and allowed to stand overnight. The violet precipitate was filtered by suction, washed with water, and dried.

TABLE I

Antiproliferative Activity against HaCaT Cells (AA), 5-LO Inhibition in Bovine PMNL (5-LO) Deoxyribose Degradation (DD), and Inhibition of Lipid Peroxidation (LPO) of 2-Substituted 1,8 Dihydroxy-9(10H)-anthracenones

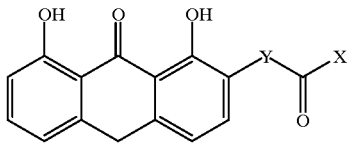

A: X=OH
B: X=OMe
C: X=NHOH
D: X=N(CH$_3$)OH

| cpd | Y | mp (° C.) | 5-LO IC$_{50}$ ($\mu$M)[a] | AA IC$_{50}$ ($\mu$M)[b] | DD ($\mu$mol of MDA/mmol)[c] | LPO IC$_{50}$ ($\mu$m)[d] |
|---|---|---|---|---|---|---|
| IA[e] | CH$_2$ | 220[g] | 22 | >5 | 3.74 ± 0.23 | |
| IB | CH$_2$ | 119 | >30 | | | |
| IC | CH$_2$ | 210[g] | 6 | | 1.89 ± 0.14 | |
| ID | CH$_2$ | 174[g] | 1 | 0.8 | 1.67 ± 0.08 | 29 |
| IIA[e] | (CH$_2$)$_2$ | 220[g] | | >5 | 2.67 ± 0.23 | |
| IIB | (CH$_2$)$_2$ | 101 | >30 | | | |
| IIC | (CH$_2$)$_2$ | | 4 | 1.3 | 1.67 ± 0.31 | |
| IID | (CH$_2$)$_2$ | 188[g] | 0.6 | 0.6 | 0.92 ± 0.03 | 11 |
| IIIA[e] | (CH$_2$)$_3$ | 201 | | >5 | 2.61 ± 0.38 | |
| IIIB | (CH$_2$)$_3$ | 123 | >30 | 1.1 | | |
| IIIC | (CH$_2$)$_3$ | 156[g] | 3 | 1.5 | 1.46 ± 0.02 | |
| IIID | (CH$_2$)$_3$ | 165[g] | 0.6 | 0.6 | 1.50 ± 0.02 | 37 |
| IVA | (CH$_2$)$_4$ | 188 | 13 | >5 | 2.62 ± 0.41 | 105 |
| IVB | (CH$_2$)$_4$ | 90 | >30 | 1.8 | 0.62 ± 0.03 | 62 |
| IVC | (CH$_2$)$_4$ | 149[g] | 2 | 2 | 1.38 ± 0.09 | 62 |
| IVD | (CH$_2$)$_4$ | 132[g] | 0.5 | 0.8 | 1.36 ± 0.05 | 16 |
| VA | (CH$_2$)$_5$ | 169 | 19 | | 2.29 ± 0.03 | |
| VB | (CH$_2$)$_5$ | 102 | >30 | | 0.13 ± 0.02 | 120 |
| VC | (CH$_2$)$_5$ | | | | | |
| VD | (CH$_2$)$_5$ | 142[g] | 0.4 | 0.9 | | 15 |
| VIA | CH=CH | | | | | |
| VIB | CH=CH | | | | | |
| VIC | CH=CH | | | | | |
| VID | CH=CH | | | | | |
| VIIA | CH$_3$CH | 209 | 17 | >5 | | |
| VIIB | CH$_3$CH | 143 | >30 | | | |
| VIIC | CH$_3$CH | 190[g] | 6 | | | |
| VIID | CH$_3$CH | 179[g] | 4 | 1.5 | 1.57 ± 0.16 | 8 |
| VIIIA | (CH$_3$)$_2$CHCH | 206[g] | 2 | >5 | 3.58 ± 0.30 | 155 |
| VIIIB | (CH$_3$)$_2$CHCH | 173 | >30 | | 0.54 ± 0.01 | 165 |
| VIIIC | (CH$_3$)$_2$CHCH | 176[g] | 6 | 1.5 | 1.66 ± 0.08 | |
| VIIID | (CH$_3$)$_2$CHCH | 156[g] | 5 | 1.5 | 0.86 ± 0.01 | 12.5 |
| IXA | PhCH$_2$CH | 225 | 1 | >5 | 3.25 ± 0.45 | |
| IXB | PhCH$_2$CH | 178 | >30 | 1.8 | 0.01 ± 0.00 | |
| IXC | PhCH$_2$CH | 168[g] | 4 | 1.5 | | |
| IXD | PhCH$_2$CH | 153[g] | 5 | 0.9 | 1.68 ± 0.13 | |
| XA | Ph(CH$_2$)$_2$CH | 140 | 2 | >5 | 2.47 ± 0.16 | 62 |
| XB | Ph(CH$_2$)$_2$CH | 119 | >30 | | 0.28 ± 0.03 | |
| XC | Ph(CH$_2$)$_2$CH | | | | | |
| XD | Ph(CH$_2$)$_2$CH | | | | | |
| XIA[f] | CH$_2$Ph-4- | | 2 | 2.6 | | |
| XIB | CH$_2$Ph-4- | | >30 | | | |
| XIC | CH$_2$Ph-4- | 194[g] | | 1.4 | | |
| XID | CH$_2$Ph-4- | 136[g] | 0.7 | 0.9 | 0.97 ± 0.03 | |
| XIIA | COPh-4- | >240[g] | 2 | >5 | 1.80 ± 0.14 | |
| XIIB | COPh-4- | 199 | >30 | 1.8 | 2.07 ± 0.12 | |
| XIIC | COPh-4- | | | | | |
| XIID | COPh-4- | | | | | |
| anthralin | | | 37 | 0.5–0.7 | 2.89 ± 0.14 | |
| Ionapalene | | | 0.5 | 3.2 | | |
| bufexamac | | | >30 | >5 | | >200 |

[a]Inhibition of 5-HETE and LTB$_4$ biosynthesis in bovine PMNL. Inhibition was significantly different with respect to that of the control, N = 3 or more, P < 0.01.
[b]Antiproliferative activity against HaCaT cells. Inhibition of cell growth was significantly different with respect to that of the control N = 3, P < 0.01.

TABLE I-continued

Antiproliferative Activity against HaCaT Cells (AA), 5-LO Inhibition in Bovine PMNL (5-LO) Deoxyribose Degradation (DD), and Inhibition of Lipid Peroxidation (LPO) of 2-Substituted 1,8 Dihydroxy-9(10H)-anthracenones

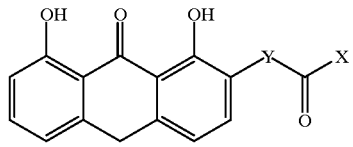

A: X=OH
B: X=OMe
C: X=NHOH
D: X=N(CH$_3$)OH

| cpd | Y | mp (° C.) | 5-LO IC$_{50}$ ($\mu$M)[a] | AA IC$_{50}$ ($\mu$M)[b] | DD ($\mu$mol of MDA/mmol)[c] | LPO IC$_{50}$ ($\mu$m)[d] |
|---|---|---|---|---|---|---|

[c]Deoxyribose degradation as a measure of hydroxyl radical formation. Indicated values are $\mu$moles of malondialdehyde per mmole of deoxyribose released by 75 $\mu$M test compound (controls < 0.1).
[d]Inhibition of AAPH-induced lipid peroxidation in bovine brain phospholipid liposomes; N = 3 or more. Nordihydroguaiaretic acid (NDGA) was used as the standard (IC$_{50}$ = 2 $\mu$M).
[e]ref Tanzer, et al., Arch Pharm (Weinheim, Ger) 321:447–449 (1988).
[f]ref Muller, et al., J. Med Chem 37:1660–1669 (1994).
[g]Decomposition.

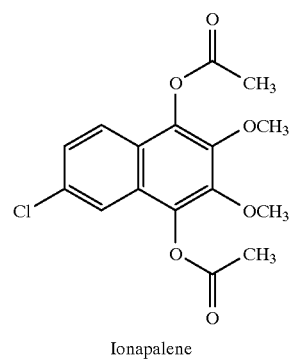

Ionapalene

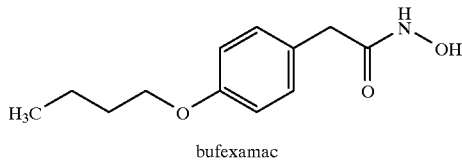

bufexamac

Several examples of preparation, biological activity and therapeutic use of the compounds and compositions of the present invention are provided below, by way of illustration and without any limitative intent.

REFERENCE EXAMPLE

For synthesis of the compounds according to the invention melting points were determined with a Büchi 510 melting point apparatus and are uncorrected. Reference to chromatography in the examples refers to column chromatography using silica gel (E. Merck, 70–230 mesh). $^1$H NMR spectra were recorded with a Varian EM 390 (90 MHz) or a Bruker Spectrospin WM 250 spectrometer (250 MHz), using tetramethylsilane as an internal standard. Fourier-transform IR spectra (KBr) were recorded on a Nicolet 510M FTIR spectrometer. UV spectra were recorded on a Kontron 810 spectrometer. Mass spectra (EI, unless otherwise stated) were obtained on a Varian MAT CH5 spectrometer (70 eV). HPLC (Kontron 420, 735 LC UV detector) was performed on a 250-×4-mm column (4-×4-mm precolumn) packed with LiChrospher 100 RP18 (5 $\mu$m) particles; (Merck, Darmstadt, Germany).

EXAMPLE 1

Synthesis of 2-substituted 1,8-dihydroxy-9(10H)-anthracenone carboxylic acid (A) by Reduction of 2-substituted 1,8-dihydroxy-9,10-anthracenone methyl carboxylate According to the method of Auterhoff, H. and Scherff, F. C. Arch Pharm (Weinheim, Ger) 293, 918–925 (1960), to a solution of each 2-substituted 1,8-dihydroxy-9,10-anthracenedione methyl carboxylate (0.30 g, 0.70 mmol) in glacial HOAc (15 mL) heated to reflux was added, dropwise over 5 hours, a solution of 40% SnCl$_2$ in 37% HCl (10 mL). The solution was then cooled, and the resulting crystals were collected by filtration, washed with water, and dried. In this manner, the following compounds were obtained:

9,10-Dihydro-1,8-dihydroxy-9-oxo-2-anthracenacetic acid (IA);

3-(9,10-Dihydro-1,8-dihydroxy-9-oxo-2-anthracene) propionic acid (IIA);

4-(9,10-Dihydro-1,8-dihydroxy-9-oxo-2-anthracene) butanoic acid (IIIA);

5-(9,10-Dihydro-1,8-dihydroxy-9-oxo-2-anthracene) pentanoic acid (IVA);

6-(9,10-Dihydro-1,8-dihydroxy-9-oxo-2-anthracene) hexanoic acid (VA);

3-(9,10-Dihydro-1,8-dihydroxy-9-oxo-2-anthracene) propenoic acid (VIA);

2-(9,10-Dihydro-1,8-dihydroxy-9-oxo-2-anthracene) propionic acid (VIIA);

2-(9,10-Dihydro-1,8-dihydroxy-9-oxo-2-anthracene)-3-methylbutanoic acid (VIIIA);

2-(9,10-Dihydro-1,8-dihydroxy-9-oxo-2-anthracene)-3-phenylpropionic acid (IXA);

2-(9,10-Dihydro-1,8-dihydroxy-9-oxo-2-anthracene)-4-phenylbutanoic acid (XA);
4-[(9,10-Dihydro-1,8-dihydroxy-9-oxo-2-anthracene)methyl]benzoic acid (XIA); and
4-[(9,10-Dihydro-1,8-dihydroxy-9-oxo-2-anthracene)oxomethyl]benzoic acid (XIIA).
Compounds IA, IIA, and IIIA are outside the scope of the invention and were prepared for comparative purposes.

EXAMPLE 2

Synthesis of 2-substituted 1,8-dihydroxy-9(10H)-anthracenone methyl carboxylate (B)

A solution of a 2-substituted 1,8-dihydroxy-9(10H)-anthraceone carboxylic acid (A) (0.5 g) in absolute methanol (50 mL) and 96% $H_2SO_4$ (0.2 mL) was refluxed for 24 hours (thin layer chromatography (TLC) control). The solution was then cooled to room temperature, treated with water (50 mL), and extracted with $CH_2Cl_2$. The organic phase was washed with water, dried over $Na_2SO_4$, and the solution evaporated. The residue was purified by chromatography using $CH_2Cl_2$. The product was treated with a small amount of hexane or petroleum ether (40-60) to induce precipitation. In this manner, the following compounds were prepared:

Methyl 9,10-Dihydro-1,8-dihydroxy-9-oxo-2-anthracenacetate (IB);
Methyl 3-(9,10-Dihydro-1,8-dihydroxy-9-oxo-2-anthracene) propionate (IIB);
Methyl 4-(9,10-Dihydro-1,8-dihydroxy-9-oxo-2-anthracene) butanoate (IIIB);
Methyl 5-(9,10-Dihydro-1,8-dihydroxy-9-oxo-2-anthracene)pentanoate (IVB);
Methyl 6-(9,10-Dihydro-1,8-dihydroxy-9-oxo-2-anthracene) hexaonate (VB);
Methyl 3-(9,10-Dihydro-1,8-dihydroxy-9-oxo-2-anthracene)propenoate (VIB);
Methyl 2-(9,10-Dihydro-1,8-dihydroxy-9-oxo-2-anthracene) propionate (VIIB);
Methyl 2-(9,10-Dihydro-1,8-dihydroxy-9-oxo-2-anthracene)-3-methylbutanoate (VIIIB);
Methyl 2-(9,10-Dihydro-1,8-dihydroxy-9-oxo-2-anthracene)-3-phenylpropionate (IXB);
Methyl 2-(9,10-Dihydro-1,8-dihydroxy-9-oxo-2-anthracene)-4-phenylbutanoate (XB);
Methyl 4-[(9,10-Dihydro-1,8-dihydroxy-9-oxo-2-anthracene)methyl]benzoate (XIB);
Methyl 4-[(9,10-Dihydro-1,8-dihydroxy-9-oxo-2-anthracene)oxomethyl]benzoate (XIIB).

Compounds XIA and XIB were prepared for comparative purposes.

EXAMPLE 3

Synthesis of 2-substituted 1,8-dihydroxy-9(10H)-antdracenonehydroxamic acid (C)

To a solution of sodium (2.07 gm 90 mmol) in absolute methanol (40 mL) was added a solution of hydroxylamine hydochloride (4.17 g, 60 mmol) in methanol (40 mL) at 0–5° C., after which the mixture was suction filtered. The filtrate was added dropwise to a suspension of a 2-substituted 1,8-dihydroxy-9(10H)-anthracenone carboxylate (B) (300 mg) in absolute methanol (15 mL) at 0–5° C. under $N_2$. The clear, yellow-orange solution was stirred until the reaction was completed (TLC control). The solution was then neutralized with 2 N HCl (pH control) and the resulting precipitate was suction filtered, washed with water, and dried. The crude product was purified by flash chromatography using $CH_2Cl_2$/methanol (90-10). In this manner each of the following compounds was prepared:

N-Hydroxy-(9,10-dihydro-1,8-dihydroxy-9-oxo-2-anthracene)acetamide (IC);
N-Hydroxy-3-(9,10-dihydro-1,8-dihydroxy-9-oxo-2-anthracene)propionamide (IIC);
N-Hydroxy-4-(9,10-dihydro-1,8-dihydroxy-9-oxo-2-anthracene)butanamide (IIIC);
N-Hydroxy-5-(9,10-dihydro-1,8-dihydroxy-9-oxo-2-anthracene)pentanamide (IVC);
N-Hydroxy-6-(9,10-dihydro-1,8-dihydroxy-9-oxo-2-anthracene)hexanamide (VC);
N-Hydroxy-3-(9,10-dihydro-1,8-dihydroxy-9-oxo-2-anthracene)propenamide (VIC);
N-Hydroxy-2-(9,10-dihydro-1,8-dihydroxy-9-oxo-2-anthracene)propionamide (VIIC);
N-Hydroxy-2-(9,10-dihydro-1,8-dihydroxy-9-oxo-2-anthracene)-3-methylbutanamide (VIIIC);
N-Hydroxy-2-(9,10-dihydro-1,8-dihydroxy-9-oxo-2-anthracene)-3-phenylpropionamide (IXC);
N-Hydroxy-2-(9,10-dihydro-1,8-dihydroxy-9-oxo-2-anthracene)-4-phenylbutanamide (XC);
N-Hydroxy-4-[(9,10-dihydro-1,8-dihydroxy-9-oxo-2-anthracene)methyl]benzamide (XIC); and
N-Hydroxy-4-[(9,10-dihydro-1,8-dihydroxy-9-oxo-2-anthracene)oxomethyl]benzamide (XIIC).

EXAMPLE 4

Synthesis of a 2-substituted 1,8-dihydroxy-9(10H)-anthracenone N-methyl hydroxamic acid (D)

According to the method of Example 2, a 2-substituted 1,8-dihydroxy-9(10H)-anthracenone methyl carboxylate (B) (300 mg) was treated with N-methylhydroxylamine hydrochloride (5.01 g, 60 mmol) until the reaction was completed (TLC control). The mixture was extracted with $CH_2Cl_2$ (2×50 Ml), and the organic phase washed with cold water (3×50 mL), dried over $NaSO_4$, and evaporated. The residue was purified by chromatography using $CH_2Cl_2$/methanol (99-1). The product was treated with a small amount of petroleum ether (40-60) at 0° C. to induce precipitation. The following compounds were prepared in this manner:

N-Hydroxy-N-methyl-(9,10-dihydro-1,8-dihydroxy-9-oxo-2-anthracene)acetamide (ID);
N-Hydroxy-N-methyl-3-(9,10-dihydro-1,8-dihydroxy-9-oxo-2-anthracene)propionamide (IID);
N-Hydroxy-N-methyl-4-(9,10-dihydro-1,8-dihydroxy-9-oxo-2-anthracene)butanamide (IIID);
N-Hydroxy-N-methyl-5-(9,10-dihydro-1,8-dihydroxy-9-oxo-2-anthracene)pentanamide (IVD);
N-Hydroxy-N-methyl-6-(9,10-dihydro-1,8-dihydroxy-9-oxo-2-anthracene)hexanamide (VD);
N-Hydroxy-N-methyl-3-(9,10-dihydro-1,8-dihydroxy-9-oxo-2-anthracene)propenarnide (VID);
N-Hydroxy-N-methyl-2-(9,10-dihydro-1,8-dihydroxy-9-oxo-2-anthracene)propionamide (VIID);
N-Hydroxy-N-methyl-2-(9,10-dihydro-1,8-dihydroxy-9-oxo-2-anthracene)-3-methylbutanamide (VIIID);
N-Hydroxy-N-methyl-2-(9,10-dihydro-1,8-dihydroxy-9-oxo-2-anthracene)-3-phenylpropionamide (IXD);
N-Hydroxy-N-methyl-2-(9,10-dihydro-1,8-dihydroxy-9-oxo-2-anthracene)-4-phenylbutanamide (XD);
N-Hydroxy-N-methyl-4-[(9,10-dihydro-1,8-dihydroxy-9-oxo-2-anthracene)methyl]benzamide (XID);
N-Hydroxy-N-methyl-4-[(9,10-dihydro-1,8-dihydroxy-9-oxo-2-anthracene)oxomethyl]benzamide (XIID).

EXAMPLE 5

Degradation of 2-deoxy-D-ribose

Degradation of deoxyribose provides a measurement of the amount of hydroxyl radical formation caused by the test compounds. The assay used to determine degradation of 2-deoxy-D-ribose followed generally the procedures of Gutteridge, J. M. C., Biochem. J., 224: 761–767 (1984) and Laughton, et al., Biochem. Pharmacol., 38: 2859–2865 (1989). The following reagents were added to glass tubes in the order and at the final concentrations listed. 0.3 mL $kH_2PO_4$—KOH buffer, pH 7.4 (30 mM), 0.2 ml double distilled $H_2O$, 0.2 ml 2-deoxy-D-ribose (2 mM), 0.2 ml $FeCl_3.6H_2O$ (0.1 mM), 0.1 ml 2-substituted anthracenone (75 µl). Stock solutions of each of the 2-substituted anthracenone compounds were made up fresh before use. Appropriate blanks and controls using an acetronitrile vehicle were performed.

Final reaction volumes were standardized to 1.0 ml. The reaction mixtures were incubated for 2 hours at 37° C. in a shaking water bath at 50 rpm. 1 ml of 2.8% (w/v) trichloracetic acid and 1 ml of 1% (w/v in 0.05 N NaOH) 2-thiobarbituric acid (TBA) were added, and the samples were heated at 100° C. for 15 minutes and then cooled in an ice bath (5 minutes). 2 ml of each reaction mixture was treated with 0.05 ml of 36% (w/v) HCl and 2 of 1-butanol, followed by vigorous shaking with a vortex mixer (Heidolph) for 15 seconds. The organic layer was separated by centrifugation at 3000 rpm (15 minutes) and absorbance at 532 nm was measured against butanol. Calibration was performed using a malondialdehyde (MDA) standard prepared by hydrolysis of 1,1,3,3-tetraethoxypropane (Gutteridge, J. M. C., Anal. Biochem., 69: 518–526 (1975). TBA reactive material was expressed in terms of µmol MDA per µmol deoxyribose. The results of the assay are provided in Table I.

EXAMPLE 6

Inhibition of Lipid Peroxidation

Phospholipids were prepared essentially as described by Gutteridge, J. M. C., (Anal. Biochem., 82: 76–82 (1977)). Bovine brain tissue was cooled on ice, freed from blood vessels and washed repeatedly with 0.15 M NaCl, pH 7.4. The tissue was cut into pieces and then macerated with an ultra-turrax, passed through a fine-meshed sieve, and extracted four times with four times the volume of acetone. The extraction mixture was filtered by suction to remove the acetone, the residue dried under vacuum, and then repeatedly extracted with petroleum ether (40-60) using twice the volume of the original brain homogenate. The combined extracts were filtered, dried at 45° C., and dissolved in ether (one fifth the original brain volume). The mixture was treated with five times the volume of acetone, and the resulting precipitate was collected by suction-filtration, dried and stored under $N_2$ at −20° C. in the dark. Bovine brain phospholipids were weighed into glass tubes and shaken in a vortex mixer (Heidolph) in the presence of five small glass beads (φ 4 mm) for 1 minute. The phospholipids were suspended in 0.15 M NaCl, pH 7.4, to a final concentration of 5 mg/ml. The mixture was purged with $N_2$ for 1 minute and vigorously dispersed in a vortex mixer for 5 minutes. The liposomes were allowed to swell for 1 hour at 4° C., and vesicles with a mean size of 1–10 µm were obtained according to the method of Bangham, et al., (J. Mol. Biol., 13:238–252 (1965). The liposomes were stimulated with the azo initiator 2 2'-azobis (2-amidinopropane) hydrochloride according to the method of Gutteridge, J. M. C., (Anal. Biochem. 82:76–82 (1977)).

The following reagents were added to the glass tubes containing stimulating bovine brain phospholipid piposomes in the order and at the final concentrations listed: 0.3 ml $HK_2PO_4$—KOH buffer, pH 7.4 (30 mM), 0.29 ml double distilled $H_2O$, 0.2 ml liposomes (1 mg/ml), 0.2 ml $FeCl_3.H_2O$ (0.1 mM), 0.01 ml 2-substituted anthracenone compound of the invention (variable concentrations).

Appropriate blanks and controls using the vehicle (acetone) were conducted. The final reaction volumes were standardized to 1.0 ml. The reaction mixtures were incubated for 1 hour at 37° C. in a shaking water bath. 10 ml of 20% (w/v) BHT, 0.5 ml 25% (w/v) HCl and 0.5 ml of 1% 2-thiobarbituric acid were added and the samples were heated at 100° C. for 15 minutes and then cooled in an ice bath (5 minutes). 2 ml of 1-butanol were added and the mixtures were vigorously shaken in a vortex mixer (Heidolph) for 15 seconds. The organic layer was separated by centrifugation at 3000 rpm (15 minutes) and absorbance at 532 nm was measured against butanol.

The results are shown in Table 1.

EXAMPLE 7

Inhibition of 5-Lipoxygenase Activity (5-LO)

Inhibition of 5-LO was determined using Ca-ionophore-stimulated bovine polymorphonuclear leukocytes (PMNL) ($10^7$ cells/ml) as described in Muller, et al., Biochem. Pharmacol., 46:1695–1704 (1993). Briefly, PMNLs were prepared from sodium EDTA-anticoagulated bovine blood, essentially as described by Walstra, P. et al., (Biochem. Biophys. Acta, 795:499–503 (1984)). Contaminating platelets were removed by repeated centrifugations at 100 g for 20 minutes. The purified PMNLs were suspended at a concentration of $1\times10^7$ cells/ml in phosphate buffered saline (PBS, composed of 8.00 g NaCl, 0.20 g KCl, 1.00 g $Na_2HPO_4.2H_2O$, 0.15 g $NaH_2PO_4.H_2O$, 0.20 g $KH_2PO_4$, adjusted to pH 7.4 with 3 $NaNH_3$ in a final volume of 1000 ml double distilled $H_2O$). Cell counts were conducted with a Sysmex micro cell counter CC-130. Preincubation was performed with 2.4 ml of the suspension and 10 µl of a DMSO stock solution of test compounds at the desired concentrations in phosphate buffered saline (PBS) or vehicle control (DMSO at final concentration of 0.4%) for 15 minutes at 37° C. in a shaking water bath at 50 rpm. The syntheses of leukotriene ($LTB_4$) and 5-lipoxygenase (5-LO) product formation was terminated by the addition of 3 ml of methanol/acetonitrile (1+1) containing nordihydroguaiaretic acid (NDGA) as free radical scavenger (final concentration 0.01 mM), and prostaglandin $B_2$ ($BGB_2$) as chromatographic marker (final concentration 0.3 µM). The incubation mixture was held on ice bath for 20 minutes and then centrifuged at 4000 g for 5 minutes at 0° C. The supernatant was diluted with 5 ml of water and passed through a prewashed (10 ml of methanol and 5 ml of water, sequentially) octadecylsilane reversed phase cartridge (Baker). The eicosanoids were eluted with 3 ml of methanol, diluted with 3 ml of water and subjected to reversed phase HPLC analysis using a 250×4 mm column packed with Nucleosil $C_{18}$ (7 µm particles; Bischoff, Leonberg, Germany). The isocratic elution conditions of $LTB_4$ were tetrahydrofuran (THF)/methanol/water/acetic acid (25+30+ 45+0.1), adjusted to pH 5.5 with concentrated $NH_3$, at a flow rate of 0.9 ml/min (Kontron 420 pump), monitored at 280 nm with a Kontron 735 LC UV detector. 5-HETE was monitored at 232 nm using methanol/water/acetic acid (77+ 23+0.1), pH 5.5 and a flow rate 1.0 ml/min. Data were recorded on a MacLab data acquisition system (WissTech, Germany) and analysis was performed using the application Peaks on an Apple Macintosh Quadra 700 computer. Integrated areas of the peaks were compared to a $PGB_2$ internal standard and to external standards of authentic samples. Molar absorption coefficients of Samuelsson et al., Borgeat, P. and B. Samuelsson, (Proc. Natl. Acad. Sci. USA, 76:2148–2152 (1979)), were used for making calculations. Inhibition was calculated by a comparison of the mean value of test compound (n=3) with control (n=6–8) activity: (1−test compound/control)×100. Inhibition was statistically significant compared to that of the control (Student's t-test: p<0.05). Each $IC_{50}$ value was derived by interpolation of a log dose vs response plot using four or more concentrations of the compound, spanning the 50% inhibition point.

By the above method, the 2-substituted anthracenones of the invention were evaluated for their ability to inhibit the production of $LTB_4$ and 5-HETE in isolated bovine PMNLs. See Walstra, P. et al., Biochem Biophys. Acta, 795:499–503 (1984); and Dannhardt et al. J. Pharm. Pharmacol., 44:419–424 (1992). $LTB_4$ and 5-HETE concentrations were measured by reversed-phase HPLC using UV detection. Table I summarizes the inhibitory potencies of the compounds as expressed by their $IC_{50}$ values. The effect of anthralin on arachidonic acid lipoxygenation was previously reported. In human neutrophils and bovine neutrophils anthralin inhibits the production of $LTB_4$ at an $IC_{50}$ value of 7–74 $\mu M$ (depending on cell density) and 37 $\mu M$, respectively. (Schroder, J. M., J. Invest. Dermatol., 87:624–629 (1986); Tanzer, et al., Arch. Pharm. (Weinheim), 324:841–846 (1991)). Several compounds of the invention had $IC_{50}$ values ranging between 0.5 and 6 $\mu M$ and were far more potent than anthralin (37$\mu$) and the hydroxyamic acid derivative, bufexemac (>30$\mu$).

A compound having a 5-LO ($IC_{50}$ ($\mu M$)) value of about 6 or less is considered to have anti-5-lipoxygenase activity.

EXAMPLE 8

Antiproliferative Activity

It has been demonstrated that in vitro cultured cell systems are useful tools in identifying new topical antipsoriatic agents, Klem, E. B., J Invest Dermatol 70, 27–32 (1978). As a model of the epidermal hyperproliferation that occurs in psoriasis HaCaT cells, a rapidly multiplying human keratinocyte cell line, which were described as an extremely sensitive target for the antiproliferative action of anthralin (Bonnekoh, et al., Arch Dermatol Res, 282:325–329 (1990)) were used to determine the effects of the compounds of this invention on cell proliferation.

HaCaT cells were grown in Dulbecco's modified Eagle's medium (DMEM, No. 041-11954A, Gibco) supplemented with 10% fetal calf serum, penicillin (100 U/mL), and streptomycin (100 $\mu$g/mL) in a humidified incubator containing 8% $CO_2$ at 37° C. Cells (2.5·10$^4$/1.1 ml per well) were seeded on 24-well multidishes and grown in DMEM. After 24 hours of growth, the medium was replaced with fresh medium and a test compound (0.1–5 $\mu M$) was added from freshly made stock solutions, which were prepared in DMSO and diluted with DMEM. The final concentration of DMSO in the culture medium was 0.2%. Controls were performed using DMSO or medium alone. Forty-eight hours after addition of a test compound to the culture, the medium was removed and each well was rinsed with phosphate-buffered saline (PBS, 100 $\mu$L). The cells were then incubated with sterile 0.5% trypsin, 0.2% EDTA in PBS for 20 minutes at 37° C. The detached cells from each well were suspended in DMEM and dispersed as single cells by gentle pipetting through an Eppendorf pipette. Cell growth was determined directly by counting the keratinocytes on a Neubauer counting chamber using phase contrast microscopy. Inhibition of cell proliferation was calculated by a comparison of the mean value of the test compound (N=3) with the control (N=6–8) activity: (1−test compound/control)×100. Inhibition was statistically significant compared to that of the control (Student's t-test; P<0.05). Each $IC_{50}$ value was derived by interpolation of a log inhibitor concentration versus response plot using four or more concentrations of the compound, spanning the 50% inhibition point.

A compound having an AA $IC_{50}$ ($\mu M$) value of less than about 5 is considered to have antiproliferative activity.

The results are shown in Table 1.

What is claimed is:

1. A compound having the structural formula

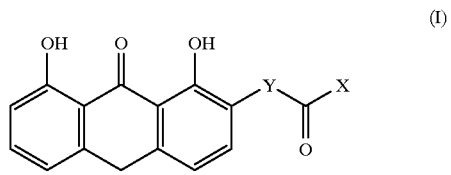

(I)

wherein

Y represents a branched chain alkylene group having 3 to 10 carbon atoms, a phenylalkylene group other than $CH_2$-Phenyl-4, having 7 to 10 carbon atoms, or a phenylacylene group having 7 to 10 carbon atoms; and X represents a hydroxyl group.

2. The compound according to claim 1 wherein said compound has a 5-LO $IC_{50}$ ($\mu M$) of less than 5.

3. The compound according to claim 1 wherein the compound has an AA $IC_{50}$ ($\mu M$) of less than 6.

4. An anti-inflammatory composition comprising a therapeutically effective amount of at least one compound according to claim 1 and a pharmaceutically or cosmetically acceptable carrier.

5. The composition according to claim 4 wherein said composition has a 5-LO $IC_{50}$ ($\mu M$) of less than 5, an AA $IC_{50}$ ($\mu M$) of less than 6 or both.

6. A compound having the structural formula

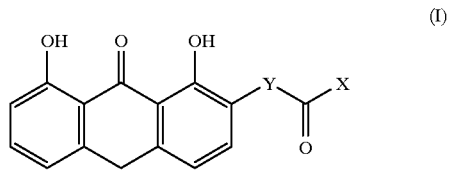

(I)

wherein

Y represents a linear or branched chain alkylene group having 1 to 10 carbon atoms, a phenylalkylene group having 7 to 10 carbon atoms, a phenylacylene group having 7 to 10 carbon atoms, an imino group, imino group substituted with a straight or branched chain alkyl group having 1 to 10 carbon atoms; and X represents an amino group, amino group substituted with a straight or branched chain alkyl group having 1 to 10 carbon atoms, a hydroxylamino group, or an N-alkyl-substituted hydroxyl amino, said N-alkyl having 1 to 10 carbon atoms.

7. The compound according to claim 6 wherein X is a hydroxylamino group or N-alkyl substituted hydroxylamino, said N-alkyl being straight or branched chain and having 1 to 10 carbon atoms.

8. The compound according to claim 7 wherein X is N-methyl hydroxylamino and Y is a straight or branched chain alkyl group having from 2 to 4 carbon atoms.

9. The compound according to claim 6 wherein Y is a linear or branched chain alkyl group having from 1 to 6 carbon atoms and X is $N(CH_3)OH$.

10. The compound according to claim 6 wherein Y is —$CH_2$ Phenyl-4 and X is $N(CH_3)OH$.

11. An anti-inflammatory composition comprising a therapeutically effective amount of at least one compound according to claim 6 and a pharmaceutically or cosmetically acceptable carrier.

12. The composition according to claim 11 wherein in said at least one compound, X represents hydroxylamino or an N-alkyl substituted hydroxylamino, said N-alkyl being straight or branched chain and having 1 to 10 carbon atoms.

13. The composition according to claim 11 wherein in said at least one compound X represents N-alkyl substituted hydroxylamino, said N-alkyl being straight or branched chain and having 1 to 10 carbon atoms and Y represents a straight or branched chain alkyl group having 2 to 4 carbon atoms.

14. The composition according to claim 11 wherein said composition has a 5-LO $IC_{50}$ ($\mu M$) of less than 5 and an AA $IC_{50}$ ($\mu M$) of less than 6.

15. The composition according to claim 11 wherein said composition comprises from about 0.01% to 10% by weight of at said at least one compound.

16. A method for treating an inflammatory condition in a patient in need thereof comprising administering to the patient a therapeutically effective amount of a composition comprising at least one compound according to claim 6 or claim 1 and a pharmaceutically acceptable carrier.

17. The method according to claim 16 comprising administering to said patient a therapeutically effective amount of a composition having a 5-LO $IC_{50}$ ($\mu M$) of less than 5, an AA $IC_{50}$ ($\mu M$) of less than 6 or both.

18. The method according to claim 16 wherein said inflammatory condition of said patient is psoriasis or contact dermatitis.

19. The method according to claim 18 wherein said composition is administered to the patient by topically applying the composition to the skin of said patient at an area in need of said treatment.

20. The method according to claim 18 wherein the composition comprises at least one compound selected from the group consisting of N-Hydroxy-N-methyl-(9,10-dihydro-1,8-dihydroxy-9-oxo-2-anthracene) acetemide; N-Hydroxy-N-methyl-3-(9,10-dihydro-1,8-dihydroxy-9-oxo-2-anthracene) propionamide; N-Hydroxy-N-methyl-3-(9,10-dihydro-1,8-dihydroxy-9-oxo-2-anthracene)-3-butanamide; N-Hydroxy-N-methyl-5-(9,10-dihydro-1,8-dihydroxy-9-oxo-2-anthracene) pentanamide; and N-Hydroxy-N-methyl-4-[(9,10-dihydro-1,8-dihydroxy-9-oxo-2-anthracene) methyl]benzamide.

* * * * *